United States Patent
Li et al.

(10) Patent No.: US 10,675,221 B2
(45) Date of Patent: Jun. 9, 2020

(54) SYSTEMS AND METHODS FOR CONTROLLING AND MONITORING MEDICATION DISPENSATION

(71) Applicant: The Regents of the University of California, Oakland, CA (US)

(72) Inventors: Guann Pyng Li, Irvine, CA (US); Sergio Gago Masague, Irvine, CA (US); Linyi Xia, Irvine, CA (US); Patricia Lim, Irvine, CA (US); Randy Li-Hung Wei, Oceanside, CA (US); Solomon Liao, Irvine, CA (US); Padma Gulur, Irvine, CA (US); Jason Kwon, Norwalk, CA (US); Xinyi Fan, Irvine, CA (US); Linh Uyen Ly, Rowland Heights, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/660,893

(22) Filed: Jul. 26, 2017

(65) Prior Publication Data

US 2018/0028408 A1    Feb. 1, 2018

Related U.S. Application Data

(60) Provisional application No. 62/366,789, filed on Jul. 26, 2016.

(51) Int. Cl.
| | |
|---|---|
| *A61J 7/04* | (2006.01) |
| *A61J 7/00* | (2006.01) |
| *G06F 19/00* | (2018.01) |
| *G16H 10/60* | (2018.01) |
| *G16H 40/63* | (2018.01) |

(Continued)

(52) U.S. Cl.
CPC ............ *A61J 7/0076* (2013.01); *A61J 7/0409* (2013.01); *A61J 7/0445* (2015.05); *G06F 19/3462* (2013.01); *G16H 10/60* (2018.01); *G16H 20/13* (2018.01); *G16H 40/63* (2018.01);

(Continued)

(58) Field of Classification Search
CPC .................................................. G07F 17/0092
See application file for complete search history.

(56) References Cited

U.S. PATENT DOCUMENTS

| | | | | |
|---|---|---|---|---|
| 5,097,982 A | * | 3/1992 | Kedem | A61J 7/0084 221/3 |
| 6,471,087 B1 | * | 10/2002 | Shusterman | A61B 5/02055 221/2 |

(Continued)

OTHER PUBLICATIONS

Lim, et al., "Looking for the Next Fix", Calit2 magazine—Interface, vol. 12, Issue 1, Fall 2016.

*Primary Examiner* — Timothy R Waggoner
(74) *Attorney, Agent, or Firm* — Thomas | Horstemeyer, LLP

(57) ABSTRACT

In one embodiment, a medication dispensing device of a system for controlling and monitoring medicine dispensation includes means for securely containing a medication to be dispensed to a specific patient, means for confirming an identify of the patient, means for determining whether or not the patient is eligible to receive a dose of the medication at a time the dose is requested, and means for dispensing the dose of medication only if the patient's identity is confirmed and the patient is eligible to receive the dose.

20 Claims, 8 Drawing Sheets

(51) Int. Cl.
*G16H 20/13* (2018.01)
*G16H 40/67* (2018.01)
*G06Q 50/22* (2018.01)
*G07F 11/62* (2006.01)

(52) U.S. Cl.
CPC .......... *G16H 40/67* (2018.01); *A61J 2200/70* (2013.01); *G06Q 50/22* (2013.01); *G07F 11/62* (2013.01)

(56) References Cited

U.S. PATENT DOCUMENTS

| | | | |
|---|---|---|---|
| 2007/0093932 A1* | 4/2007 | Abdulhay | A61J 7/0084 700/231 |
| 2009/0167531 A1* | 7/2009 | Ferguson | G06F 19/3462 340/572.1 |
| 2010/0253476 A1* | 10/2010 | Poutiatine | A61J 7/0053 340/10.1 |
| 2010/0318218 A1* | 12/2010 | Muncy, Jr. | G06F 19/3462 700/220 |
| 2013/0090594 A1* | 4/2013 | Palmer | A61J 7/0053 604/60 |
| 2014/0277702 A1* | 9/2014 | Shaw | G06F 19/3462 700/232 |

* cited by examiner

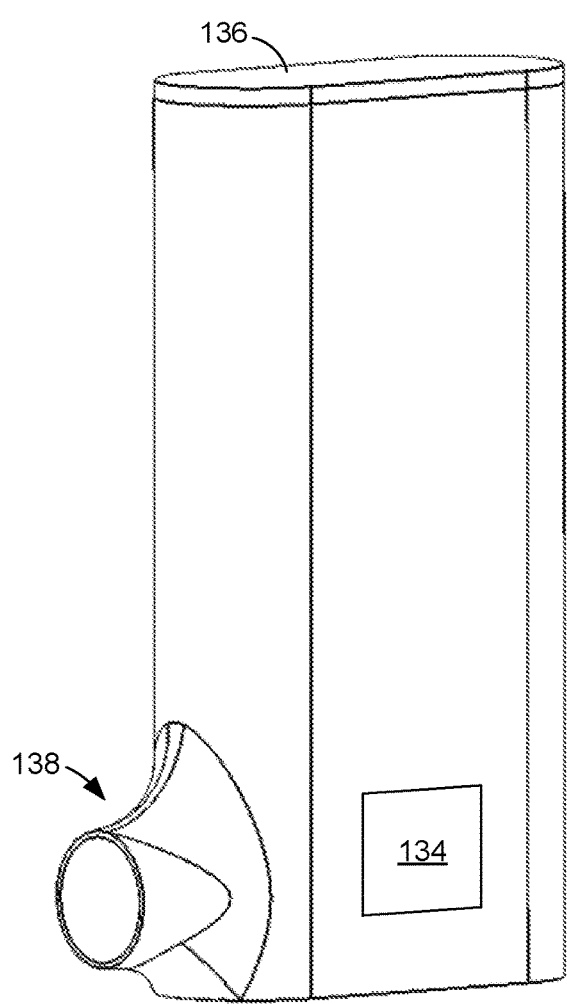
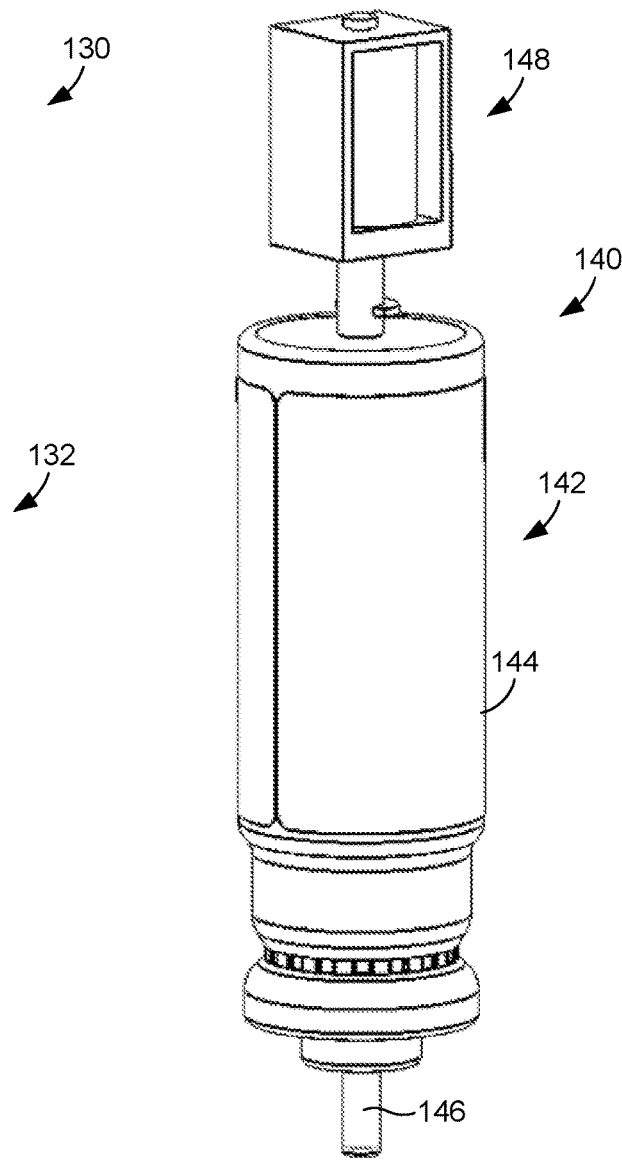
FIG. 8
FIG. 9

SYSTEMS AND METHODS FOR CONTROLLING AND MONITORING MEDICATION DISPENSATION

CROSS-REFERENCE TO RELATED APPLICATION

This application claims priority to U.S. Provisional Application Ser. No. 62/366,789, filed Jul. 26, 2016, which is hereby incorporated by reference herein in its entirety.

BACKGROUND

Prescription controlled substance misuse, abuse, and diversion are major public health problems in the United States. Opioids are one example of such a substance. In 2013, prescription opioids were responsible for more deaths than from suicide and motor vehicle accidents combined. Despite this fact, the number of prescription opioids in the United States continues to rise due to healthcare provider's perceived benefits of opioids for chronic symptom, decreased social stigma associated with prescription opioids, and healthcare provider fear of undertreating symptoms resulting in poor healthcare provider satisfaction scores and litigation. The major challenges for healthcare providers are reducing opioid misuse, abuse, and drug diversion while ensuring patient safety and therapeutic response to opioid therapy.

The American Society of Interventional Pain Healthcare providers' opioid guideline in management of chronic non-cancer pain recommends pill counting by healthcare providers to reduce misuse and drug diversion by ensuring that patients are taking the medication at the agreed upon dosing and timing, and that there are no missing pills suggesting theft or sale of opioids. However, performing pill counting for all patients is resource and time intensive for medical practices. As a result, pill counting is performed randomly, infrequently, or not at all.

There is no device in the market that meets all the needs described above. Medication event monitor systems have improved the health-related outcomes (i.e., lowered blood pressure, reduced hospital and emergency room visits) of patients with hypertension, heart failure, human immunodeficiency virus (HIV), and epilepsy by improving medication adherence with audible and visual reminders and recording the date and time of every bottle cap opening. The disadvantages of such systems are that patients can take multiple pills with each bottle cap opening, misuse the prescription, overdose, and have pills stolen. Current systems cannot prevent theft, dispense one pill at a time, count pills, or modulate dispensing frequency as per the prescription. As such, there is no way of monitoring medication adherence using existing technology.

From the foregoing discussion, it can be appreciated that it would be desirable to have a system and method for controlling and monitoring the dispensation of medication.

BRIEF DESCRIPTION OF THE DRAWINGS

The present disclosure may be better understood with reference to the following figures. Matching reference numerals designate corresponding parts throughout the figures, which are not necessarily drawn to scale.

FIG. 8 is a perspective view of a further embodiment of a medication dispensing device that can be used in a system for controlling and monitoring medication dispensation.

FIG. 9 is a perspective view of an embodiment of a medication dispensing mechanism that can be used in the medication dispensing device of FIG. 8.

DETAILED DESCRIPTION

As described above, it would be desirable to have a system and method that can be used to control and monitor the dispensation of medication. Disclosed herein are systems and methods designed for this purpose. These systems and methods include a medication dispensing device that is provided to a patient (end user) or care giver and that is configured to dispense medication to the patient and record various data concerning the use and operation of the device, such as when medication is requested by the patient and when it is dispensed to the patient. In some embodiments, the device incorporates security that prevents dispensation to anyone but the person to whom the medication is prescribed and incorporates an algorithm that prevents medication from being administered beyond healthcare provider-prescribed intervals. In some embodiments, the device is configured to transmit the data it collects to the patient's healthcare provider to enable him or her to track the patient's medication usage. Analysis can be performed on this data to assist the healthcare provider in tailoring a treatment plan that is best for the patient.

In the following disclosure, various specific embodiments are described. It is to be understood that those embodiments are example implementations of the disclosed inventions and that alternative embodiments are possible. All such embodiments are intended to fall within the scope of this disclosure.

Figure 1:
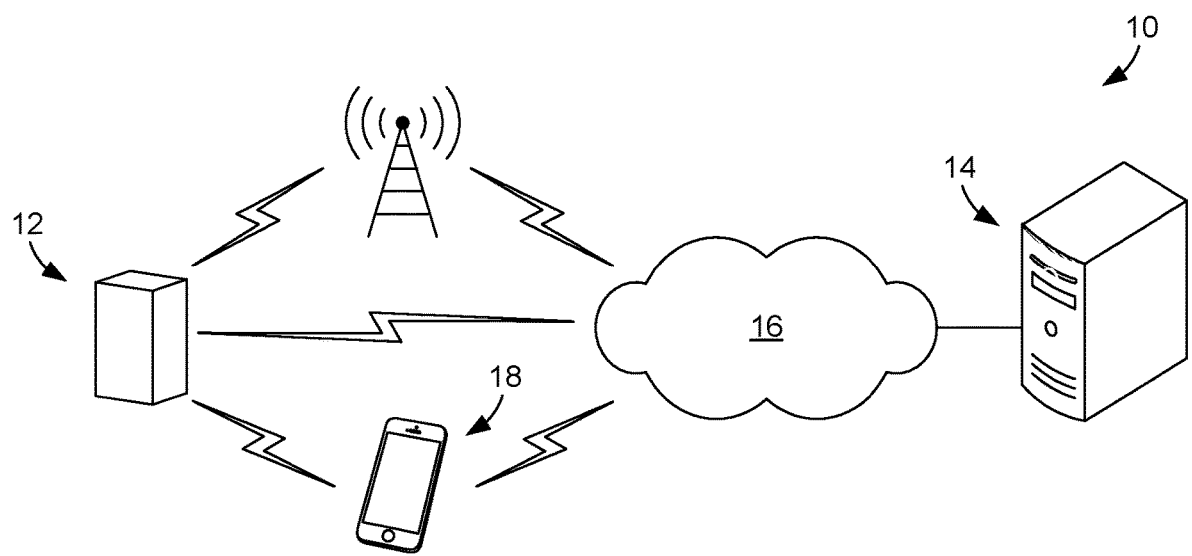
FIG. 1 is a schematic diagram of an embodiment of a system for controlling and monitoring medication dispensation.

FIG. 1 illustrates an example system 10 for controlling and monitoring medication dispensation. The system 10 includes a medication dispensing device 12 that can be provided to a patient when a medication is prescribed to the patient by a healthcare provider. As will be described in greater detail below, the device 12 is configured to securely contain the medication and is further configured to only dispense the medication, in the prescribed dosage, to the patient once the identity of the patient has been verified. In addition, the device 12 is configured to only dispense the medication to the patient if an appropriate time interval has passed since the last time a dose was administered and only if the prescribed maximum daily dosage has not been reached. In addition, the device 12 is configured to log various data about the use and operation of the device, such as when medication was requested by the patient and when medication was dispensed to the patient.

As suggested by FIG. 1, the medication dispensing device 12 is also configured to transmit data to a remote healthcare provider computing device 14 so that the data collected by the dispensing device can be shared with the patient's healthcare provider and analyzed. This data can be communicated to the healthcare provider computing device 14 in a variety of ways. For example, the data can be wirelessly transmitted directly to a computer network 16 using a suitable wireless technology, such as WiFi, and then delivered to the healthcare provider computing device 14. Alternatively or in addition, the data can be wirelessly transmitted to the network 16 using a mobile telephony technology, such as a cellular phone network. Alternatively or in addition, the data can be wirelessly transmitted to the network 16 using a mobile device 18, such as a mobile phone, owned or operated by the patient. In such a case, the data can be wirelessly transmitted to the mobile device 18 using a suitable wireless technology, such as WiFi, cellular, or Bluetooth, and the mobile device can then forward the data to the network 16.

Irrespective of the method with which the data is transmitted to the healthcare provider computing device 14, the data can be transmitted in real time as certain events occur or on an intermittent (e.g., periodic) basis. It is further noted that, although various wireless transmission methods have been identified, the data can, in some embodiments, be transmitted to the healthcare provider computing device 14 using a wired connection, for instance, when the patient visits the healthcare provider's office.

Figure 2:
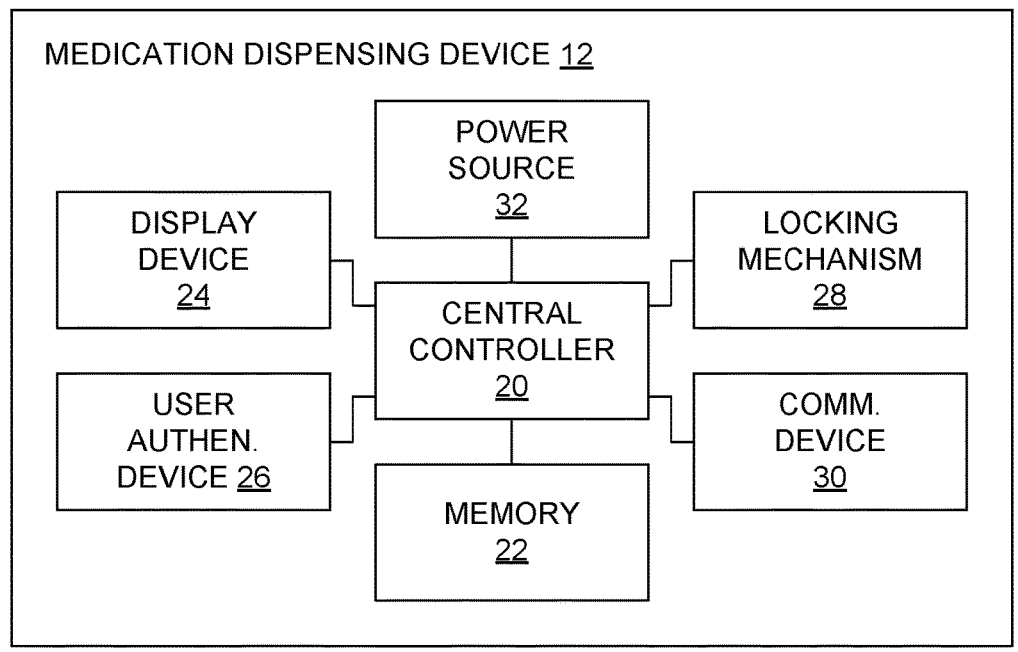
FIG. 2 is a block diagram illustrating an example of electrical components that a medication dispensing mechanism shown in FIG. 1 can have.

FIG. 2 is a block diagram that identifies various electrical components that the medication dispensing device 12 can comprise. As shown in this figure, the device 12 can comprise a central controller 20 that includes a processing device, such as a microprocessor, that is configured to execute computer instructions that control the operation of the device. The device 12 further comprises non-volatile memory 22, which can either be part of or independent from the central controller 20. The memory 22 can store the aforementioned computer instructions, in the form of one or more computer programs and/or algorithms, and further can be used to store the data that is recorded during use and operation of the device 12. The device 12 further can include a display device 24 that can be used to display information to the patient and, when the display device is touch-sensitive, receive patient inputs.

With further reference to FIG. 2, the medication dispensing device 12 can also comprise a user authentication device 26 that can be used to confirm the identity of the patient before medication is dispensed. As described below, such an authentication device 26 can, in some embodiments, comprise one or more biometric sensors. Further included in the device 12 is a locking mechanism 28 that prevents medication from being dispensed to anyone but the patient and that ensures that medication is only dispensed to the patient within the prescribed intervals. The example device 12 of FIG. 2 also includes one or more communication devices 30 that are used to communicate data to another device, such as the healthcare provider computing device 14. As noted above, the communication devices 30 can be configured to transmit the data wirelessly and/or over a wired connection. The medication dispensing device 12 can further include a power source 32, such as a battery, that powers the various electrical components of the device. Such a battery can, in some embodiments, be rechargeable. In some embodiments, the device 12 can further be configured to plug into a power outlet to obtain the power required for the device to operate.

Figure 3:
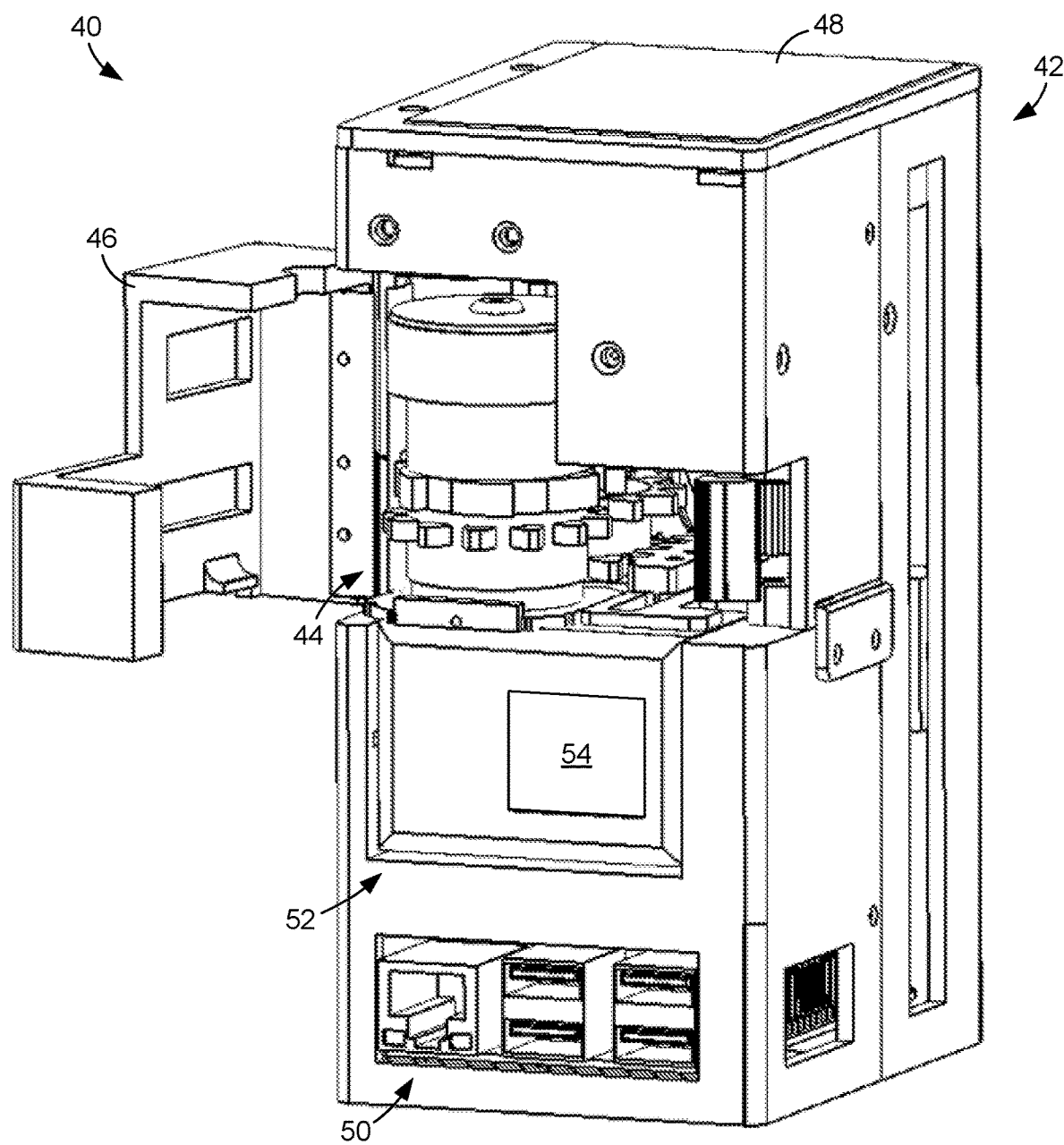
FIG. 3 is a perspective view of an embodiment of a medication dispensing device that can be used in a system for controlling and monitoring medication dispensation.

FIG. 3 illustrates an example embodiment of a portable, hand-held medication dispensing device 40 that can be used in a system for controlling and monitoring medication dispensation, such as system 10. In this embodiment, the device 40 is specifically configured to dispense medications in pill form. It is noted, however, that, in other embodiments, the device 40 can be configured to dispense medication in other forms, such as in a liquid form or an aerosol form. As shown in FIG. 3, the medication dispensing device 40 comprises an outer housing 42 that contains and protects the various internal components of the device, including an internal medication dispensing mechanism 44 that is visible when a hatch 46 of the housing is open. This mechanism 44 is discussed in detail in relation to FIGS. 4 and 5 below. In some embodiments, the housing is sized and configured so as to be easily held in the patient's hand or hands and to be easily transported from place to place.

With further reference to FIG. 3, visible on the exterior of the medication dispensing device 40 is a display device 48 that, in the embodiment of FIG. 3, is provided on the top of the device. As indicated above, the display device 48 can be used to display various information to the patient. This information can include an identification of a status of the device (on/off, battery level, etc.), the medication(s) the device contains, the dosage(s) of the medication(s) that have been prescribed, the identity and contact information of the prescribing healthcare provider, the quantity of medication (e.g., number of pills) remaining within the device, the time the medication was last dispensed to the patient, the time at which a further dose can next be dispensed to the patient, and any other information that may be of benefit to the patient. In embodiments in which the display device 48 is a touch screen display, it can further be used by the patient to input information into the device. Such information can, for example, include a passcode, information as to pain levels (e.g., a pain score from 1-10), information as to any side effects that are being experienced, or any other information that may be useful to the healthcare provider in determining how best to treat the patient.

As is also shown in FIG. 3, the medication dispensing device 40 can further include one or more communication ports 50 that enable the device to communicate with another device, such as the healthcare provider computing device 14 (FIG. 1), for the purpose of transmitting data to and/or receiving data from the other device. The transmitted data can be that identified above in relation to FIG. 2 and the received data can be that provided by the healthcare provider to adjust the manner in which medication is administered to the patient, such as dosage, dispensing intervals, and the like. In some embodiments, the communication ports 50 can include an Ethernet port and one or more universal serial bus (USB) ports. These ports 50 can, in some embodiments, be mounted to a printed circuit board (PCB) to which the central controller 20 and the other electrical components can be mounted.

Integrated into the housing 42 of the medication dispensing device 40 is a medication dispensing drawer 52 that can move from a closed position shown in FIG. 3 in which the medication is not accessible to an open position in which the medication can be accessed and taken by the patient. As described in greater detail below, the dispending drawer 52 can be configured to linearly extend outward from the housing 42 to provide a single dose (e.g., single pill) of the medication to the patient once the patient has been authenticated and it has been confirmed by the device 40 that the patient is eligible to receive the dose. In some embodiments, the dispensing drawer 52 comprises a medication well (see FIG. 5) in which pills can be received, the well only being accessible to the patient when the dispensing drawer is in the open position.

As is also shown in FIG. 3, a user authentication device, in the form of a biometric sensor 54 can be integrated into the medication dispensing drawer 52. The sensor 54 can be configured to collect any biometric information that can be used to authenticate the identity of the patient before medication is dispensed. Such a sensor 54 can, for example, comprise a fingerprint sensor, a retina or face scanner (camera), a voice recognition component (microphone), or any other device capable of collecting biometric information. Such information can be compared to biometric information stored within memory of the device 40. As described below, this stored biometric information can be obtained in an initialization procedure prior to normal use of the device 40 by the patient. In some embodiments, the biometric sensor 54 can comprise a device that integrates one or several laboratory functions on a single integrated circuit, i.e., a lab-on-a-chip. In such cases, blood can be provided by the patient and analyzed to provide further information to the device 40 that can be used for authentication purposes and/or for determining whether or not medication should be dispensed to the patient given the current status of the patient as determined by the analysis of the patient's blood.

Figure 4:
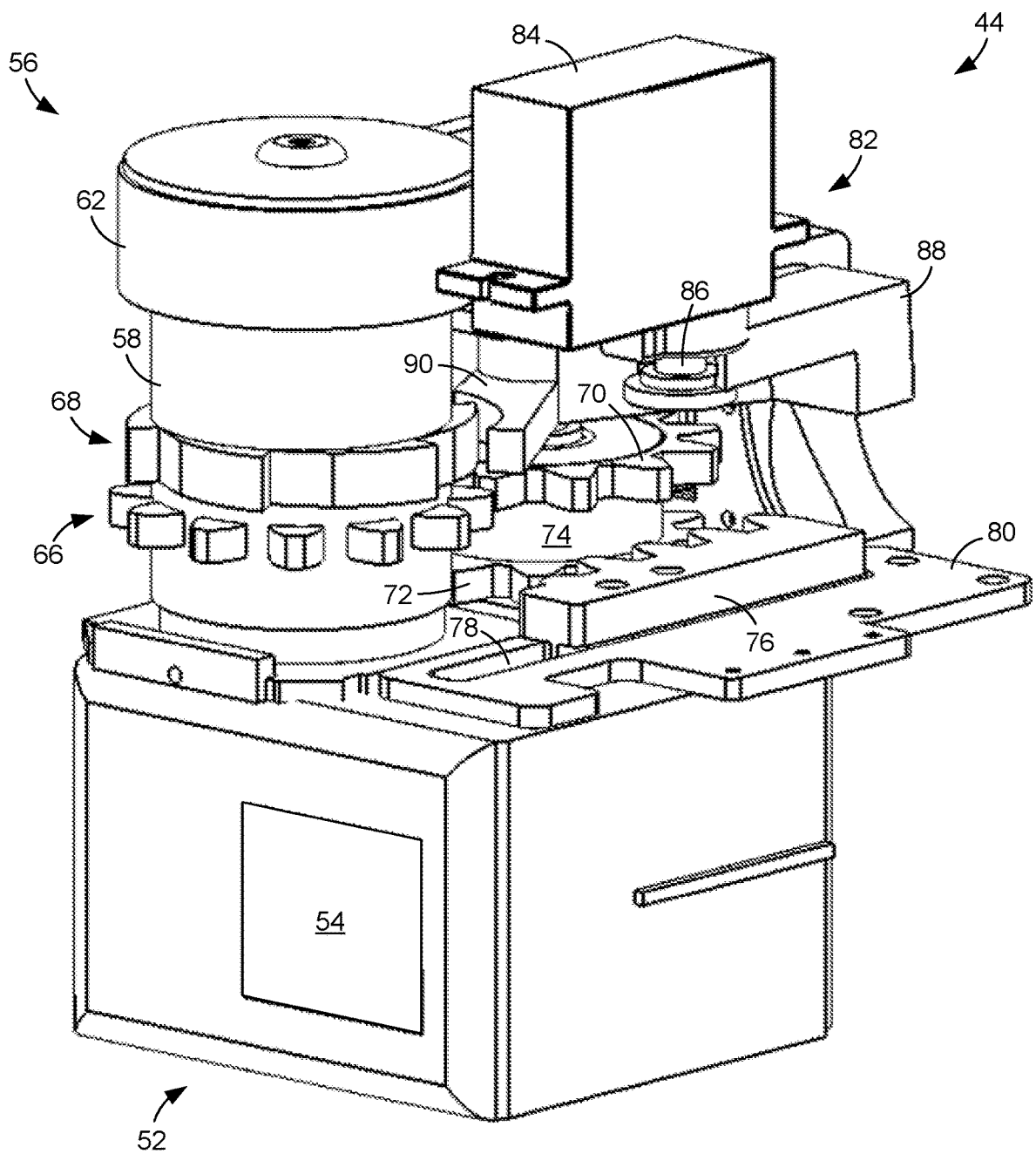
FIG. 4 is a perspective view of an embodiment of a medication dispensing mechanism that can be used in a medication dispensing device.
Figure 5:
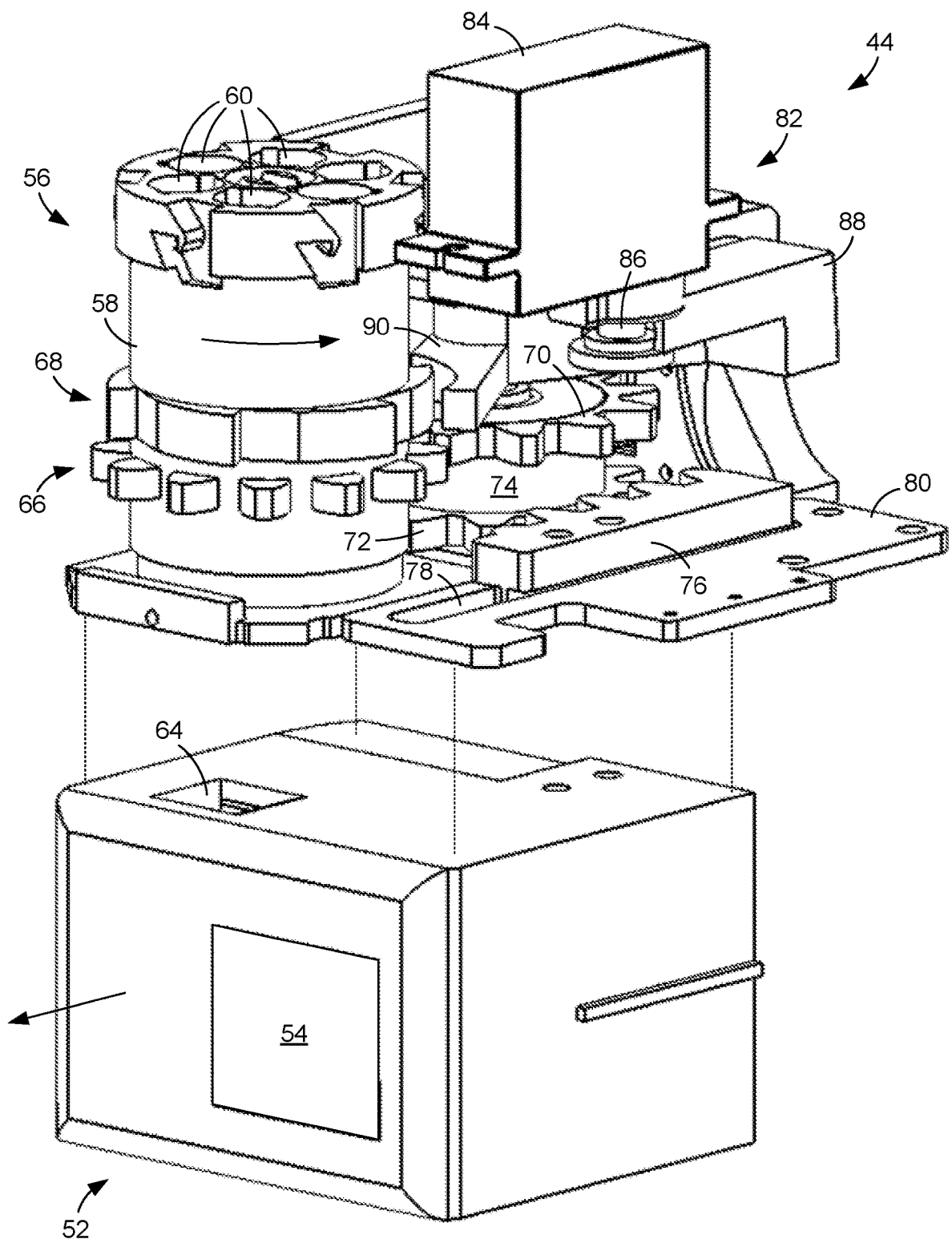
FIG. 5 is a further perspective view of the medication dispensing mechanism shown in FIG. 4.

FIGS. 4 and 5 illustrate the medication dispensing mechanism 44 and the medication dispensing drawer 52 independent of the remainder of the medication dispensing device 40. With reference first to FIG. 4, the mechanism 44 includes a rotatable medication cylinder 56 that is positioned in close proximity to (e.g., directly above) the dispensing drawer 52. This cylinder 56 includes a body 58 that, as shown in FIG. 5, includes multiple elongated vertical chambers 60 in which medication can be stored. As shown in FIG. 4, these chambers 60 are covered by a cap 62 that, in some embodiments, comprises coil springs (not shown) that push the pills within their chambers downward toward the medication dispensing drawer 52. As illustrated in FIG. 5, which shows the dispensing drawer 52 separated from the mechanism 44, the drawer can include a well 64 provided in its top surface with which the chambers 60 can alternately align so as to maintain a single pill in the well for dispensation. As is shown in both FIGS. 4 and 5, the body 58 of the cylinder 56 includes gear teeth 66 that can be used to rotate the cylinder and ratchet teeth 68 that can be used to inhibit rotation of the cylinder. The uses of these teeth 66, 68 are described below in the discussion of the operation of the mechanism 44.

With continued reference to FIGS. 4 and 5, the medication dispensing mechanism 44 further includes a first gear 70 having teeth that engage the gear teeth 66 of the medication cylinder 56. The first gear 70 is coupled to a second gear 72 with a one-way bearing 74. As described below, the bearing 74 only enables the first gear 70 to rotate with the second gear 72 in the clockwise direction such that the cylinder 56 can only rotate in the counterclockwise direction, which advances the cylinder so as to align a next chamber 60 with the well 64 of the medication dispensing drawer 52. Also included in the mechanism 44 is a gear rack 76 having teeth that engage the teeth of the second gear 72. The rack 76 is fixedly mounted to the medication dispensing drawer 52 such that the drawer can only move from the closed position to the open position and vice versa when the rack can linearly travel along a track 78 formed in a plate 80 of the mechanism 44.

As is also shown in FIGS. 4 and 5, the medication dispensing mechanism 44 further includes a locking mechanism 82 that prevents the medication drawer 52 from moving from the closed position to the open position when the dispensation of medication is not authorized. In the illustrated embodiment, the locking mechanism 82 includes an actuation device 84, such as a servomotor, that is controlled by the central controller of the medicine dispensing device 40. The actuation device 84 includes a shaft 86 to which a lever 88 is mounted. When the actuation device 84 is actuated, the lever 88 be can moved into or out of contact with a pawl 90. As described below, when the mechanism 82 is locked, the lever 88 is pivoted so as the urge the pawl 90 into contact with the cylinder 56 such that the pawl engages the ratchet teeth 68 and prevents rotation of the cylinder which, thereby, prevents the dispensing drawer 52 from opening. When the locking mechanism 82 is unlocked, however, the lever 88 is moved to a position that enables the pawl 90 to move out of contact with the ratchet teeth 68 (e.g., under the force of a spring) and therefore enables rotation of the cylinder 56 as well as linear translation of the medication drawer 52 to the open position.

An example of use and operation of the system for controlling and monitoring medication dispensation will now be discussed. When a patient visits a healthcare provider's office and a determination is made that the patient is to be prescribed a medication, particularly one that is often abused and/or stolen and whose dispensation should be carefully controlled, the healthcare provider can prescribe a medication dispensing device along with the prescribed medication. The medication dispensing device can be filled with the prescribed medication by the healthcare provider's office, a pharmacy, or other responsible entity. In an embodiment such as that shown in FIGS. 3-5, this can entail filling one or more of the chambers 60 of the medication cylinder 56 with one or more types of pills that have been prescribed to the patient and correctly aligning the cylinder relative to the medication dispensing drawer 52.

When the filled device is provided to the patient, the patient can be instructed as to how to use it. In addition, the medication dispensing device can be configured for use only by the patient by collecting biometric information of the patient that will be used later to authenticate the patient when a request for medication is received. For example, when the medication dispensing device uses a fingerprint to authenticate the patient, the patient can be prompted to press a finger against a fingerprint sensor of the device during a device initialization procedure. It is noted that biometric information can be collected with another device that can communicate with the medication dispensing device. For example, if the patient's mobile phone is capable of scanning a fingerprint, the patient can have his or her fingerprint scanned by the phone, and the phone can communicate to the medication dispensing device whether or not the fingerprint is a match. In cases in which the patient is uncomfortable with sharing biometric information, the patient can alternatively be requested to input a passcode or other unique identifier that the patient has selected to confirm his or her identity. In such a case, this information can, for example, be entered using a touch screen display of the medication dispensing device. Notably, such a passcode can be stored on the device even when biometric information is stored on the device as a failsafe.

Before the medication dispensing device is released to the patient, relevant information regarding the medication and how it is to be used can be downloaded to or input into the device. Such information can comprise the type of information that is typically provided on the label of a pill bottle, such as the name of the medication the device contains, the dosage of the medication that has been prescribed (e.g., amount and frequency), the identity and contact information for the prescribing healthcare provider, the quantity of medication (e.g., number of pills) contained within the device, and the like.

Once the medication dispensing device has been set up for use by the patient, the patient can take the device home and use it to obtain the prescribed medication. When the patient wishes the device to dispense medication, the user can convey this intention to the device. For example, in embodiments in which the medication dispensing device includes a biometric sensor, the patient can provide his or her biometric information to the device (e.g., press his or her finger against the sensor). In some embodiments, the medication dispensing device by default operates in a sleep mode to limit power consumption. When the patient interacts with the device to provide the biometric information (e.g., presses his or her finger on the sensor), this action can wake the device at which point the device will then acquire the biometric information (e.g., read the fingerprint) and compare it to the biometric information that was stored during the initialization procedure. Alternatively, if the medication dispensing device has been configured to receive a passcode to authenticate the patient, the patient can press the touch-sensitive display to wake up the device and then enter the passcode when prompted to do so.

If the authentication information provided by the patient is a match for the information stored in the device, a determination will next be made by the device as to whether or not the medication can be dispensed to the patient at the present time. By way of example, this determination can depend upon whether enough time has passed since the last time medication was dispensed to the patient. For example, if the medication is a pain medication that is only to be taken with a frequency of up to every four hours, the medication dispensing device will not dispense further medication to the patient if medication had been dispensed only three hours ago. In such a case, the device can convey the reason why the medication will not be dispensed to the patient using the display device. For example, the dispensing device can indicate that it is not yet time to receive the medication and identify the time at which medication can again be taken. In addition, the medication dispensing device can determine that medication cannot be dispensed if a daily maximum dosage has already been reached for that day.

Assuming the patient is authenticated by the medication dispensing device and that the patient is eligible to receive medication at the time of the request, the device will dispense medication to the patient. In an embodiment such as that illustrated in FIGS. 3-5, the lever 88 of the locking mechanism 82 can be pivoted away from the pawl 90 using the actuation device 84 (under the control of the central controller) so as to enable the pawl to disengage from the ratchet teeth 68 provided on the medication cylinder 56. When this occurs, the cylinder 56 can then rotate in the counterclockwise direction (see curved arrow in FIG. 5) and does so because of the engagement between the gear teeth 66 and the first gear 70, which is connected to the second gear 72, which is engaged with the gear rack 76, which is connected to the medication dispensing drawer 52. Because the cylinder 56 is free to rotate, springs (not shown) that act on the medication drawer 52 are able to push the drawer outward from the medication dispensing device 40 (see straight arrow in FIG. 5) so as to expose the medication well 64 and a pill that had previously been loaded into the well.

At this point, the patient can remove the pill from the well 64 and then push the medication dispensing drawer 52 back into the medication dispensing device 44 to return it to its original closed position. Notably, rotation of the cylinder 56 as the drawer dispensing 52 moves to the open position causes the next chamber 60 to align with the well 64 once the drawer is pushed back to the closed position. As such, the well 64 is loaded with a pill from a chamber 60 of the medication cylinder 56 each time the dispensing drawer 52 is moved to the open position. Therefore, the device 40 is again ready to dispense a pill when it is permissible to do so. Notably, the cylinder 56 does not rotate as the dispensing drawer 52 is pushed back into the medication dispensing device 40 because of the one-way bearing 74, which enables the second gear 72 (associated with the drawer) to rotate without rotating the first gear 70 (associated with the cylinder). Once the dispensing drawer 52 is returned to the closed position by the patient, the drawer and the cylinder 56 are again locked by the locking mechanism 82. In particular, the lever 88 is pivoted by the actuation device 84 so as to urge the pawl 90 into engagement with the ratchet teeth 68 of the cylinder 56, so as to prevent the cylinder 56 from rotating and, thereby, prevent that dispensing drawer 52 from opening.

As the patient uses the medication dispensing device, irrespective of its configuration, the device records data regarding this use. For example, the device can record the fact that the patient requested medication and at what time, the duration of time that had passed since the previous time the patient had requested medication, and whether or not medication was or was not dispensed. In addition, other data can be recorded by the medication dispensing device. This data can, in some embodiments, comprise patient-reported feedback. For example, when medication is a pain medication, the device can prompt the patient to identify his or her current pain levels, e.g., by entering a pain score from 1-10, when the medication is requested. This pain information can further be used to determine whether or not medication will be dispensed and/or what particular dosage of the medication will be dispensed. For instance, a first, lower dosage of a pain medication may be dispensed to the patient if the patient reports a pain score of 1-5, while a second, higher dosage of pain medication may be dispensed if the patient reports a pain score of 6-10. In the embodiment of FIGS. 3-5, these different dosages of medication can be contained in alternative chambers 60 of the medication cylinder 56. Notably, the medication dispensing device can prompt the patient to enter such pain information after a pain medication has been administered (e.g., two hours after dispensation) to collect information that may be useful to the prescribing healthcare provider in gauging the effectiveness of the medication.

It is also noted that, in some embodiments, the medication dispensing device can be configured to remind the patient when it is time to take his or her next dose. For example, the device can provide a visual and/or audible alert to the patient when the required amount of time has elapsed since the last time medication was dispensed. In other embodiments, the device can comprise software that is configured to track patterns associated with the patient's medication usage and symptoms (e.g., pain levels and advise the patient to take the medication before his or her symptoms reach an extreme level. With such a feature, such extreme pain can be avoided before it occurs. Such software can comprise one or more machine-learning algorithms that make these determinations. In such a case, the software can operate in an initial training mode for a period of time to learn and analyze the patient patterns.

Irrespective of the particular data that is collected by the medication dispensing device, the data can be provided to the healthcare provider, for example, by wirelessly transmitting it to a computing device owned or operated by the healthcare provider or the healthcare provider's office. As noted above, data can be wireless transmitted either in real time as it is collected by the device or intermittently. In other embodiments, the data can be transmitted to the healthcare provider computing device using a wired connection, for example, when the patient returns to the healthcare provider's office for a follow-up visit. Once the data is received, it can be stored in association with the patient. For example, the data can be entered into the patient's electronic medical records so that it will be available to the healthcare providers involved in the patient's care in tracking the patient's usage of the medication as well as determining whether changes should be made in the patient's treatment.

Software that resides on the healthcare provider's computing device, or that can be accessed by the healthcare provider, can be used to analyze the data for the purpose of improving patient care. In some embodiments, this software can incorporate machine learning to assist the healthcare provider in determining what and how much medication to administer to the patient based upon information such as a frequency with which the patient requests medication, the medication strength, and the feedback (e.g., pain levels) reported by the patient. In some embodiments, the software can further make suggestions to the healthcare provider as to changes in the administration of medication based upon the various data that has been collected. If any changes are to be made regarding the manner in which the medication is administered, instructions can be downloaded to the medication dispensing device. For example, if it is determined that a particular medication should be administered more often, the device can be reconfigured to enable medication to be dispensed every three hours instead of every four hours. It is also noted that the data collected by numerous medication dispensing devices provided to numerous patients can be analyzed together to draw global conclusions as to particular medications and their usage by patients. In still further embodiments, the software can issue alerts to the healthcare provider when the patient is not taking the medication as prescribed to prompt the healthcare provider to follow up with the patient.

It is noted that other functionalities can be incorporated into the system and/or the medication dispensing device. For example, the medication dispensing device can be configured to only dispense medication when the device is connected to a trusted network. If the device is lost, the patient can report this and the device can be automatically locked and the location of the device (if determinable) can be provided to the patient and/or the patient's healthcare provider. In addition, any information stored on the device, such as biometric information and patient identity, can be automatically erased from the device. In other embodiments, the medication dispensing device can have connection expansion capabilities. For example, the device can be configured to require network-based verification (internet or local connections via radio frequencies).

In other embodiments, additional patient data can be collected either by the medication dispensing device or by another device used by the patient. For example, the healthcare provider software can integrate activity data (e.g., steps take, accelerometer data, stairs climbed, miles walked, etc.) and biometric data (e.g., heart rate, oxygen saturation in blood, etc.) collected with a wearable body monitor (e.g., smart watch) or mobile device (e.g., mobile phone). The time-series data from the other devices can be correlated with use of the medication dispensing device.

In still other embodiments, the patient can be required to provide further information and/or perform particular tasks before medication will be dispensed. For example, the medication dispensing device can be configured to require the patient to perform a simple task, such as matching pictures displayed in the display device, before medication will be dispensed. If the patient is unable to perform the task correctly at the time of the medication dispensation request (e.g., due to intoxication or a mental impairment), the request can be denied and an explanation provided as to why. When such additional information or task is required, it can either be required intermittently, for example, on a randomized basis, or can be required each time a medication dispensation request is received.

Figure 6:
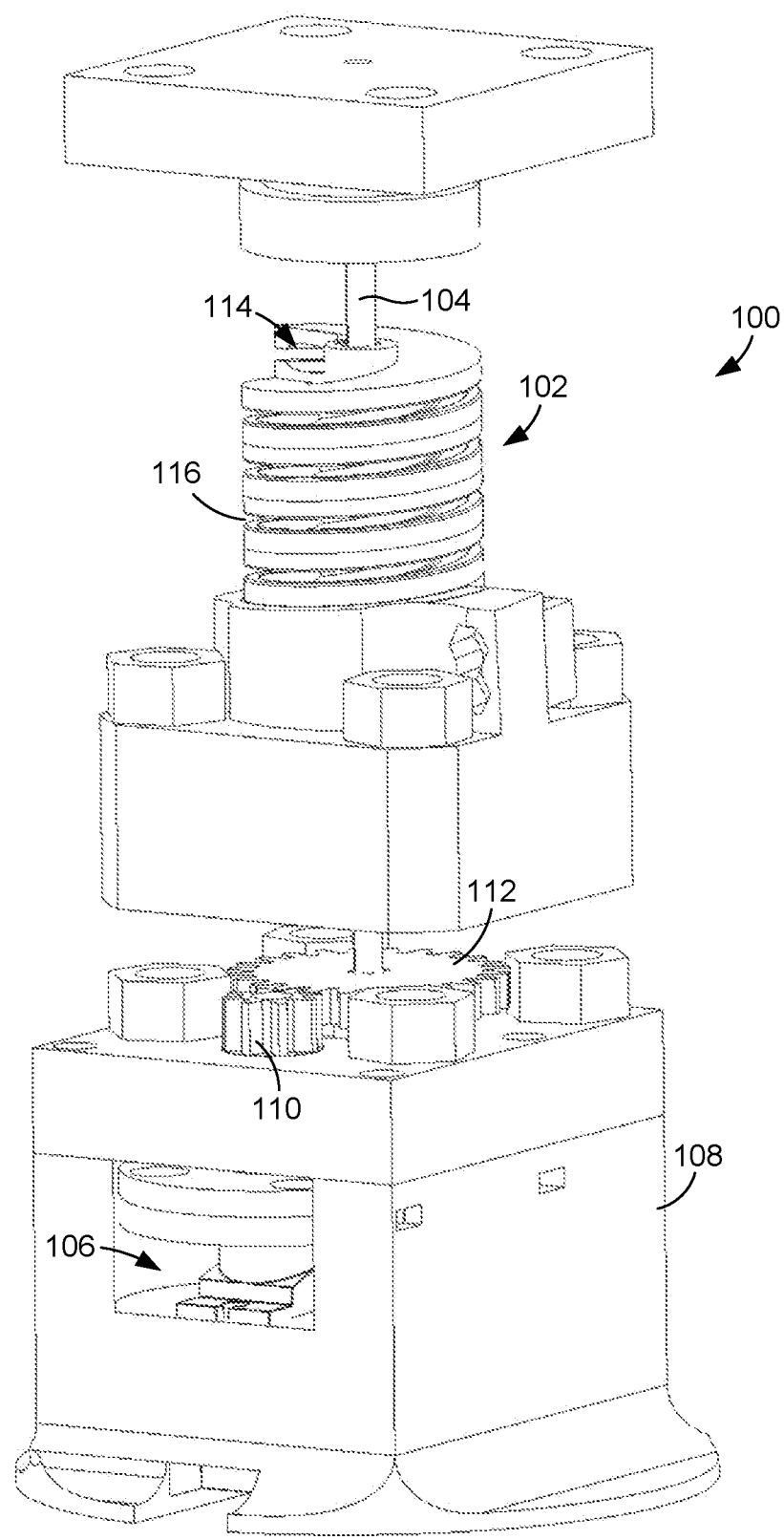
FIG. 6 is a perspective view of an alternative embodiment of a medication dispensing mechanism that can be used in a medication dispensing device.
Figure 7:
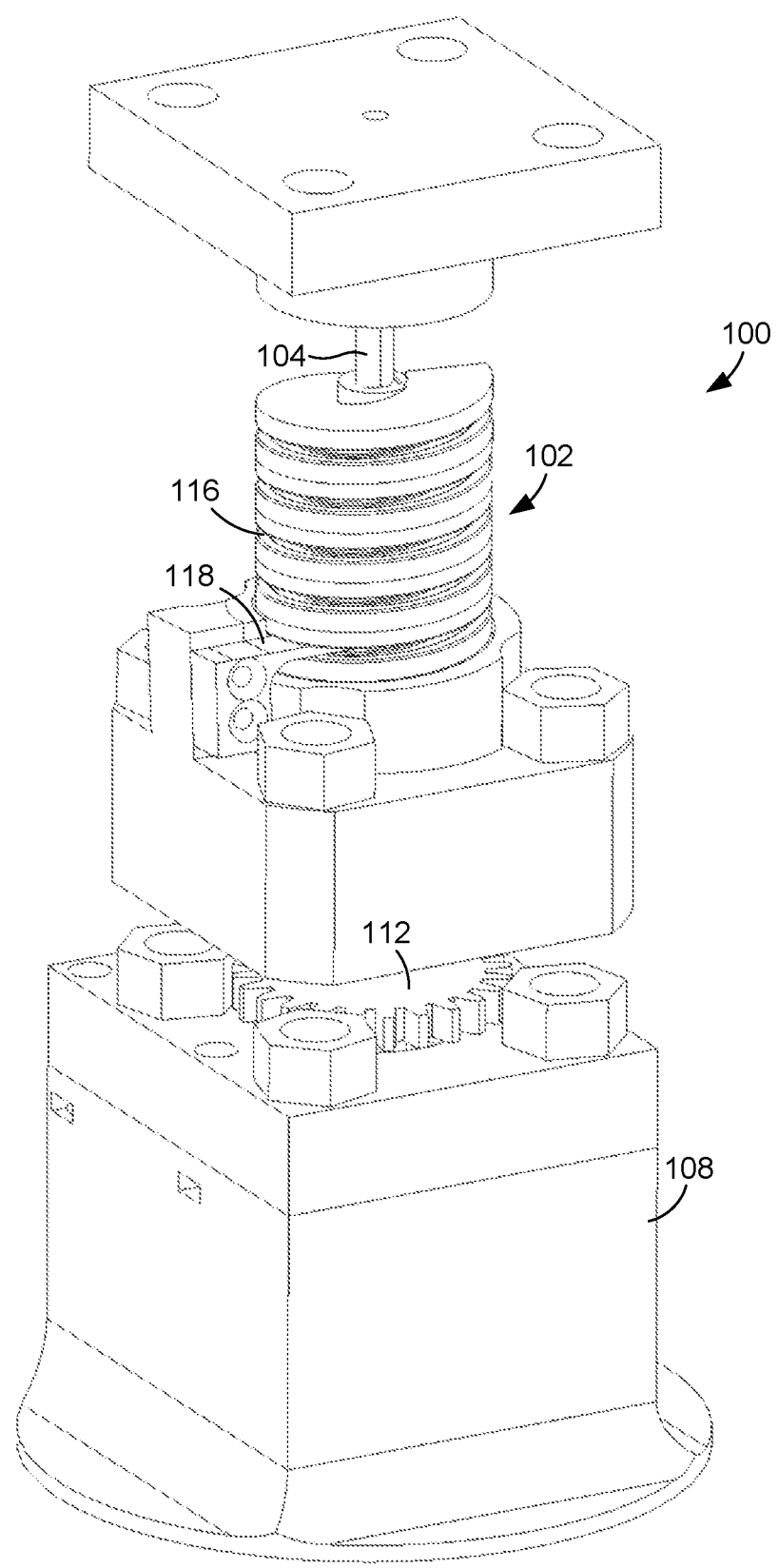
FIG. 7 is a further perspective view of the medication dispensing mechanism shown in FIG. 6.

In the medication dispensing device embodiment of FIGS. 3-5, the medication dispensing mechanism 44 comprised a medication cylinder 56 from which pills can be dispensed. FIGS. 6 and 7 show an alternative medication dispensing mechanism 100 that can be used in a medication dispensing device. Instead of using a cylinder having multiple chambers, the mechanism 100 uses a helical storage member 102 from which medication can be dispensed. With reference to FIG. 6, the helical storage member 102 configured as a helical coil that is mounted to a shaft 104 that can be rotated in the counterclockwise direction with an actuation device 106, such as a servomotor, that is contained in housing 108. When the actuation device 106 is activated under the control of the central controller of the medication dispensing device in which the mechanism 100 is used, the actuation device rotates a first gear 110, which in turn rotates a second gear 112, which is mounted to the shaft 104.

As is apparent in FIGS. 6 and 7, the helical storage member 102 comprises an inner helical passage 114 that extends along the length of the member in which pills to be dispensed can be provided. Extending from the helical passage 114 to an outer edge of the member 102 along the length of the member is a helical slot 116. As shown in FIG. 7, a fixed dispensing arm 118 extends through the helical slot 116 and into the helical passage 114 so that the arm can interface with the pills contained within the member 102.

Prior to use of the medication dispensing device that comprises the medication dispensing mechanism 100, pills are loaded into the helical storage member 102 so that they are aligned back-to-back within the helical passage 114 from a bottom end of the member 102 from which pills are dispensed to the dispensing arm 118. When a pill is requested by the patient from the medication dispensing device and dispensation of the pill is authorized, the actuation device 106 rotates the helical storage member 102 counterclockwise. As the helical storage member 102 rotates relative to the fixed dispensing arm 118, a pill is forced out of the bottom end (i.e., outlet) of the member as the force applied by the arm to the top-most pill is transmitted from pill to pill along the line of pills. A single pill can then drop into a medication well provided on or in the medication dispensing device so that it can be accessed and taken by the patient. In some embodiments, the outlet of the helical storage member 102 comprises one or more resilient retaining elements, such as an O-ring (not shown) that only enables a pill to pass through the outlet when a predetermined level of force is applied to the pill. This prevents accidental dispensation of medication. It is also noted that the degree to which the helical storage member 102 is rotated (i.e., the angle through which the member rotates) is coordinated with the size (e.g., length) of the pill such that only one pill will be dispensed when the motor 106 is activated and so that a next pill in the line is positioned at the outlet and is prepared for dispensing.

As mentioned above, the medication dispensing device can be configured to dispense medication in forms other than pill form. FIG. 8 illustrates a medication dispensing device 130 that is configured to dispense medication in aerosol form (i.e., a gas-propelled spray of fine droplets of liquid medicine). Like the device 40 shown in FIG. 3, the device 130 includes an outer housing 132 that contains the various internal components of the device, including electrical components described above. Integrated into the housing 132 is a biometric sensor 134, such as a fingerprint sensor, and a display device 136, such as a touch screen display. In addition, however, the housing 132 incorporates a nozzle 138 from which aerosolized medication can be ejected for administration to a patient.

FIG. 9 shows an example embodiment for a medication dispensing mechanism 140 that can be contained within the housing 132 of the medication dispensing device 130. As illustrated in FIG. 9, the mechanism 140 includes a removable and replaceable medication cartridge 142. The cartridge 142 includes a canister 144 that contains pressurized liquid medication that is to be administered to the patient in aerosol form. Extending from the canister 144 is a nozzle 146 from which the aerosolized medication can be ejected.

In contact with the medication cartridge 142 is an actuation device 148 that is configured to move the canister 144 relative to the nozzle 146. More specifically, the actuation device 144 is configured to linearly displace the canister 144 downward toward the nozzle 146. When the canister 144 is displaced in this manner, the nozzle 146 is temporarily pushed into the canister and a predetermined volume of aerosolized medication is ejected from the nozzle. In some embodiments, the actuation device 148 comprises a solenoid actuator that actuates when determined to do so by a central controller of the medication dispensing device 130.

The medication dispensing device 130 can be used and operated in similar manners to the medication dispensing device 44 described above. Accordingly, the patient can convey a desire to receive medication (e.g., by pressing a finger against the biometric sensor 134), the device 130 can authenticate the patient and confirm that the patient is eligible to receive the medication, and, assuming the patient's identity and eligibility are confirmed, dispense the medication. In this case, the patient can place the nozzle 138 in his or her mouth and receives the medication orally.

Figure 10:
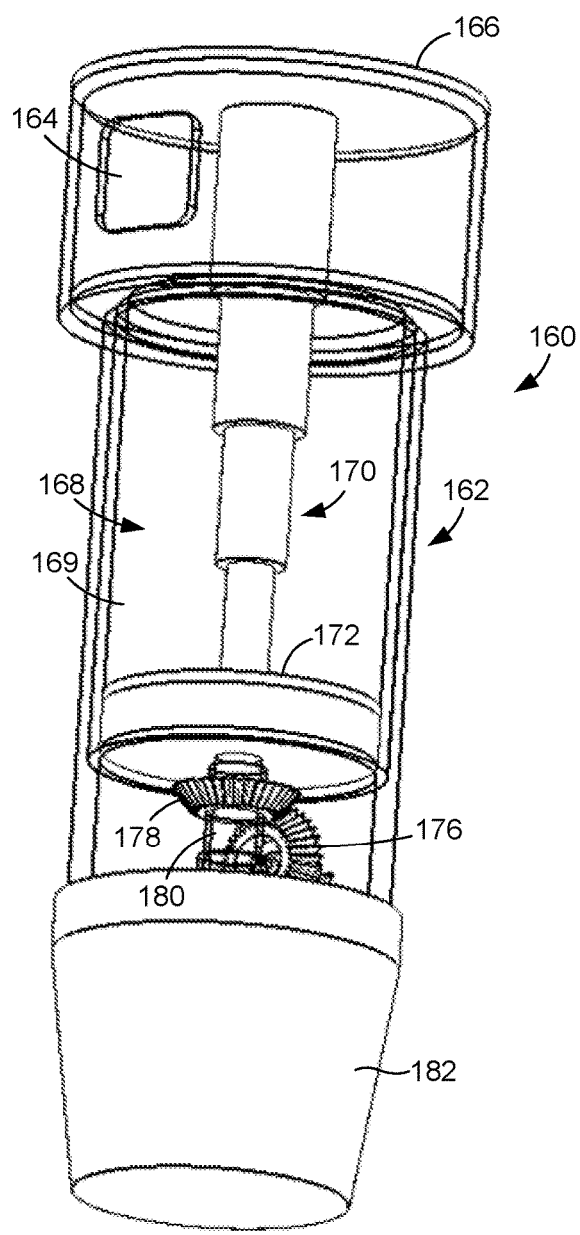
FIG. 10 is a perspective view of a further embodiment of a medication dispensing device that can be used in a system for controlling and monitoring medication dispensation.
Figure 11:
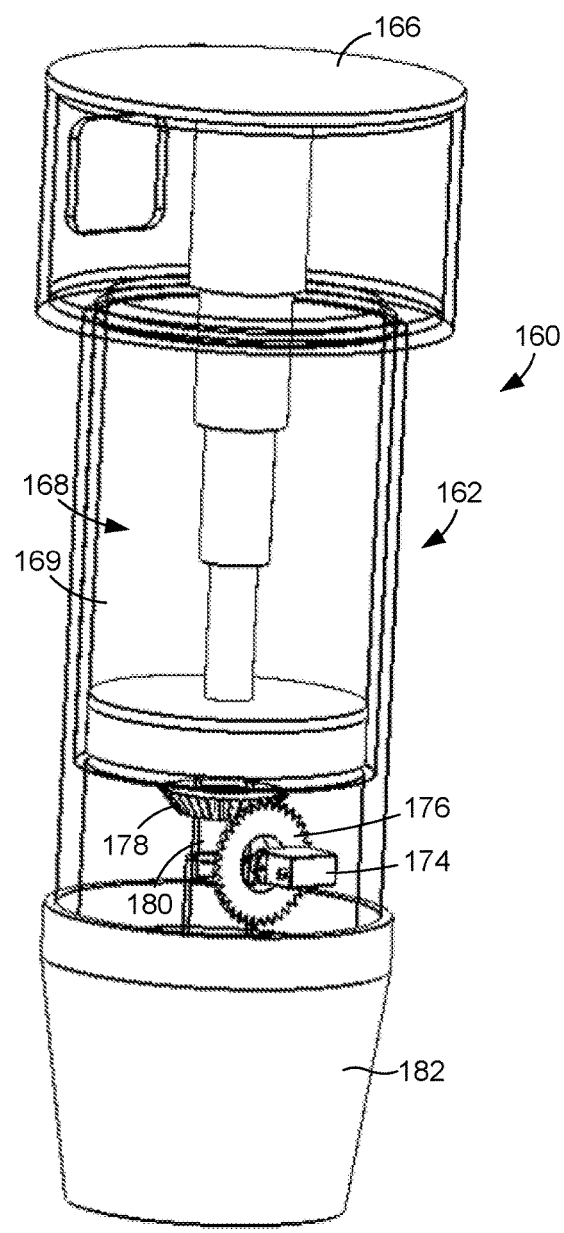
FIG. 11 is a further perspective view of the medication dispensing device of FIG. 10.

In addition to pills and aerosolized medication, a medication dispensing device can be configured to dispense liquid medication. FIGS. 10 and 11 show an example of such a medication dispensing device 160. The device 160 also includes an outer housing 162 that contains the various internal components of the device. Integrated into the housing 162 is a biometric sensor 164, such as a fingerprint sensor, and a display device 166, such as a touch screen display.

Contained within the housing 160 is a medication dispensing mechanism 168. In the embodiment of FIGS. 10 and 11, the mechanism 168 includes a reservoir 169 in which the liquid medication can be stored. Provided in the reservoir 169 is a telescopic shaft 170 to which is mounted a plunger 172. Positioned adjacent the plunger 172 is an actuation device 174 (FIG. 11), such as a servomotor, that can drive a first gear 176 that is engaged with a second gear 178. The actuation device 174 can cause the first gear 174 to rotate when commanded to do so by a central controller of the medication dispensing device 160. The rotation of the first gear 176 causes rotation of the second gear 178, which drives the plunger 172 upward within the reservoir 169 so as to drive a predetermined volume of liquid medication through an exit tube 180 that extends from the reservoir. Medication ejected from the tube 180 drops down into a detachable cup 182 from which the patient can drink the medication. In some embodiments, the mechanism 168 can include a twist valve that prevents leakage.

The medication dispensing device 160 can also be used and operated in similar manners to the medication dispensing device 44. Accordingly, the patient can convey a desire to receive medication (e.g., by pressing a finger against the biometric sensor 164), the device 160 can authenticate the patient and confirm that the patient is eligible to receive the medication, and, assuming the patient's identity and eligibility are confirmed, dispense the medication into the cup 182.

The invention claimed is:

1. A medication dispensing device comprising:
means for securely containing a medication to be dispensed to a specific patient, the means for securely containing a medication comprising a rotatable medication cylinder that includes multiple chambers each configured to hold multiple pills that can be dispensed;
means for confirming an identify of the patient;
means for determining whether or not the patient is eligible to receive a dose of the medication at a time the dose is requested; and
means for dispensing the dose of medication only if the patient's identity is confirmed and the patient is eligible to receive the dose, the means for dispensing the dose of medication comprising a medication dispensing mechanism including a normally locked medication dispensing drawer having a pill well configured to receive one pill at a time from the rotatable medication cylinder, the means for dispensing further comprising a locking mechanism configured to unlock the medication dispensing drawer to enable it to open for the patient only when the patient's identity is confirmed and the patient is determined to be eligible to receive the dose, wherein the medication dispensing drawer is configured to be closed by the patient after the pill is removed from the pill well and wherein closing of the drawer causes rotation of the rotatable medication cylinder, which enables a new pill to be transferred from the cylinder to the pill well of the drawer so as to load the drawer with the next dose of medication.

2. The medication dispensing device of claim 1, wherein the means for securely containing a medication comprises an outer housing.

3. The medication dispensing device of claim 1, wherein the means for confirming an identity of the patient comprises a biometric sensor.

4. The medication dispensing device of claim 3, wherein the biometric sensor comprises a fingerprint sensor.

5. The medication dispensing device of claim 1, wherein the means for determining whether or not the patient is eligible comprises a central controller that executes a software program configured to determine when the last time medication was dispensed by the medication dispensing device.

6. The medication dispensing device of claim 1, further comprising means for storing data regarding use and operation of the medication dispensing device.

7. The medication dispensing device of claim 1, wherein the means for storing data is configured to store at least a date and time each time medication is requested and a date and time each time medication is dispensed.

8. The medication dispensing device of claim 7, wherein the means for storing data is further configured to store patient feedback received from the patient.

9. The medication dispensing device of claim 7, further comprising means for transmitting the stored data to a remote computing device for remote storage and analysis.

10. The medication dispensing device of claim 1, further comprising means for conveying information to the user.

11. The medication dispensing device of claim 10, wherein the means for conveying information comprises a touch screen display with which information can be visually communicated to the patient and with which information can be input by the patient.

12. The medication dispensing device of claim 1, wherein the locking mechanism comprises an actuation device configured to lock and unlock the rotatable medication cylinder.

13. The medication dispensing device of claim 12, wherein the actuation device is a servomotor.

14. The medication dispensing device of claim 12, wherein the actuation device is configured to move a locking element into and out of contact with teeth provided on the rotatable medication cylinder, wherein contact between the locking element and the teeth prevents rotation of the cylinder.

15. The medication dispensing device of claim 14, wherein the medication dispensing mechanism further comprises gears that only enable the medication dispensing drawer to open when the rotatable medication cylinder rotates.

16. A system for controlling and monitoring medication dispensation, the system comprising:
   a medication dispensing device including:
   (a) means for securely containing a medication to be dispensed to a specific patient, the means for securely containing a medication comprising a rotatable medication cylinder that includes multiple chambers each configured to hold multiple pills that can be dispensed,
   (b) means for confirming an identify of the patient,
   (c) means for determining whether or not the patient is eligible to receive a dose of the medication at a time the dose is requested,
   (d) means for dispensing the dose of medication only if the patient's identity is confirmed and the patient is eligible to receive the dose, the means for dispensing the dose of medication comprising a medication dispensing mechanism including a normally locked medication dispensing drawer having a pill well configured to receive one pill at a time from the rotatable medication cylinder, the means for dispensing further comprising a locking mechanism configured to unlock the medication dispensing drawer to enable it to open for the patient only when the patient's identity is confirmed and the patient is determined to be eligible to receive the dose, wherein the medication dispensing drawer is configured to be closed by the patient after the pill is removed from the pill well and wherein closing of the drawer causes rotation of the rotatable medication cylinder, which enables a new pill to be transferred from the cylinder to the pill well of the drawer so as to load the drawer with the next dose of medication, and
   (e) means for transmitting data regarding use and operation of the medication dispensing device to a remote computing device; and
   a remote computing device that executes software configured to receive and analyze the data transmitted by the medication dispensing device.

17. The system of claim 16, wherein the software is configured to determine whether or not the patient's prescription should be changed.

18. A method for controlling and monitoring medication dispensation, the method comprising:
   securely containing a medication to be dispensed to a specific patient, the means for securely containing a medication comprising a rotatable medication cylinder of a medication dispensing device that includes multiple chambers each configured to hold multiple pills that can be dispensed
   the medication dispensing device confirming an identify of a patient;
   the medication dispensing device determining whether or not the patient is eligible to receive a dose of the medication at a time the dose is requested;
   the medication dispensing device dispensing the dose of medication only if the patient's identity is confirmed and the patient is eligible to receive the dose, wherein dispensing the dose of medication comprises unlocking a normally locked medication dispensing drawer of the device and opening the drawer to provide the patient with access to a pill well of the drawer that is configured to receive one pill at a time from a rotatable medication cylinder of the medication device, wherein the medication dispensing drawer is configured to be closed by the patient after the pill is removed from the pill well and wherein closing of the drawer causes rotation of the rotatable medication cylinder, which enables a new pill to be transferred from the cylinder to the pill well of the drawer so as to load the drawer with the next dose of medication; and
   the medication dispensing device transmitting data regarding use and operation of the medication dispensing device to a remote computing device for storage and analysis.

19. The method of claim 18, wherein the medication dispensing device confirming an identity of a patient comprises the medication dispensing device receiving biometric information and comparing it with stored biometric information.

20. The method of claim 18, wherein the medication dispensing device determining whether or not the patient is eligible to receive a dose of a medication comprises the medication dispensing device determining when the last time medication was dispensed by the medication dispensing device.

* * * * *